United States Patent [19]

Fraser et al.

[11] 4,443,539

[45] Apr. 17, 1984

[54] PROCESS FOR PREPARING BOVINE GROWTH HORMONE

[75] Inventors: Thomas H. Fraser, Kalamazoo; Barbara J. Bruce, Portage, both of Mich.

[73] Assignee: The Upjohn Company, Kalamazoo, Mich.

[21] Appl. No.: 271,449

[22] Filed: Jun. 8, 1981

Related U.S. Application Data

[63] Continuation-in-part of Ser. No. 119,037, Feb. 5, 1980, abandoned.

[51] Int. Cl.$^3$ .................. C12N 15/00; C12N 1/18; C12N 1/20; C12P 21/00; C12R 1/19; C12R 1/865

[52] U.S. Cl. .................... 435/68; 435/172; 435/253; 435/256; 435/317; 435/849; 435/942

[58] Field of Search .............. 435/68, 172, 91, 317, 435/253, 942, 849, 256

[56] References Cited

U.S. PATENT DOCUMENTS

| | | | |
|---|---|---|---|
| 4,237,224 | 12/1980 | Cohen et al. | 435/68 |
| 4,332,898 | 1/1982 | Reusser | 435/317 |
| 4,338,400 | 7/1982 | Manis et al. | 435/317 |
| 4,340,674 | 7/1982 | Manis et al. | 435/317 |

FOREIGN PATENT DOCUMENTS

| | | | |
|---|---|---|---|
| 11562 | 5/1980 | European Pat. Off. | 435/172 |
| 2033905 | 5/1980 | United Kingdom | 435/172 |

OTHER PUBLICATIONS

Keshet et al., Chemical Abstracts, 94:117615m, p. 359, Apr. 13, 1981.
Loi et al., P.N.A.S., 77(1), 244–248 (1980).
Hamer et al., Nature, 281, 35–40 (1979).
Beggs, Nature, 275, 104–109 (1978).
Struhl et al., PNAS, 73(5), 1471–1475 (1976).
Lemke, *Viruses and Plasmids in Fungi*, Marcel Dekker, Inc., New York, 588–589 (1979).
Itakura, K. et al., Science 198:1056–1063 (1977).
Proc. Natl. Acad. Sci. (1978) 75:5936–5940, Fraser et al.

*Primary Examiner*—Esther M. Kepplinger
*Attorney, Agent, or Firm*—Roman Saliwanchik

[57] ABSTRACT

A process for expression of the gene for bovine growth hormone in the yeast *Saccharomyces cerevisiae*. Bovine growth hormone can be used to increase milk production in cows.

4 Claims, 1 Drawing Figure

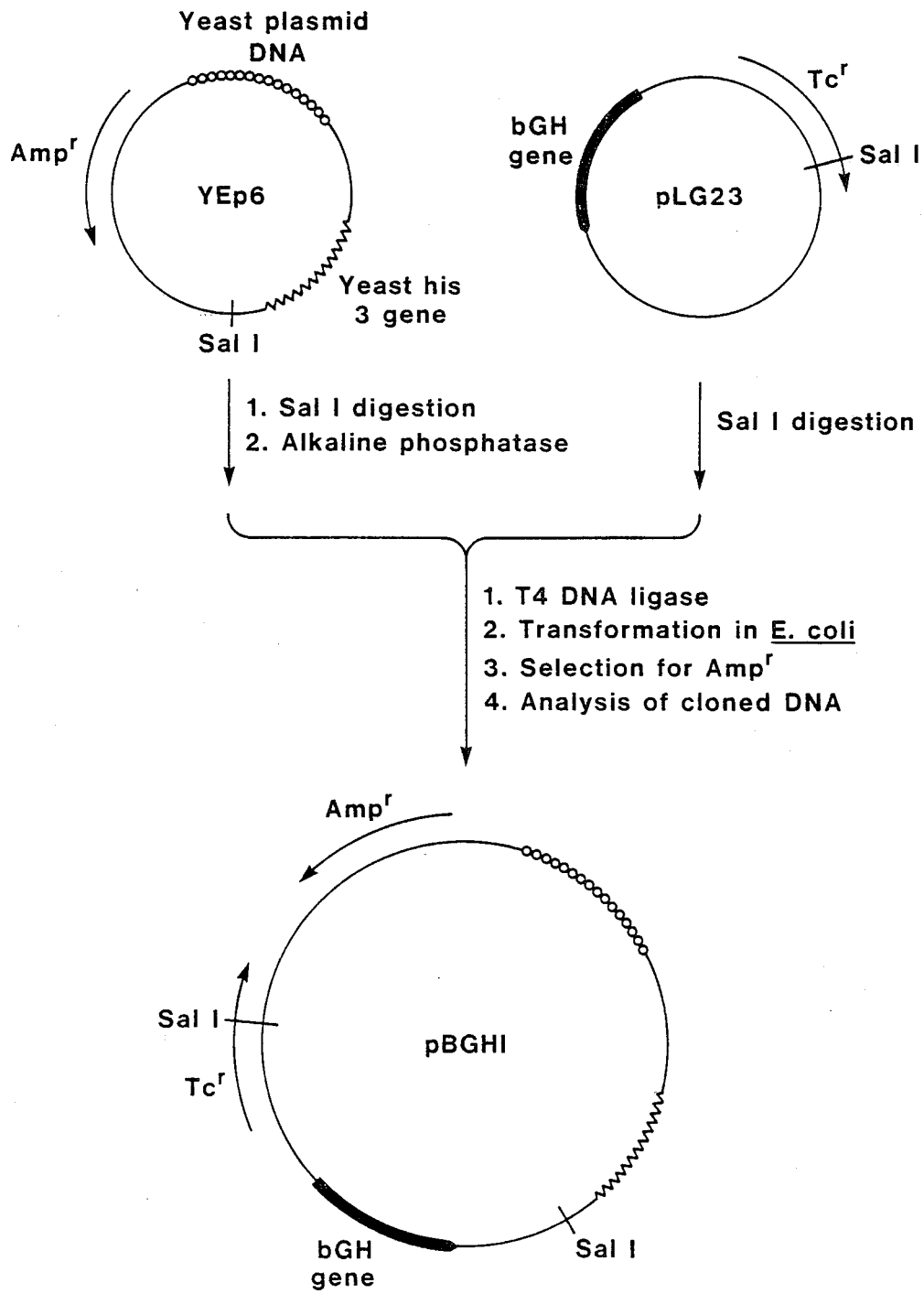

PROCESS FOR PREPARING BOVINE GROWTH HORMONE

DESCRIPTION

Cross Reference to Related Application

This application is a continuation-in-part of our pending application Ser. No. 119,037, filed on Feb. 5, 1980, now abandoned.

BACKGROUND OF THE INVENTION

Many of the potential benefits envisioned as a result of the application of recombinant DNA technology to medical problems require the insertion into host organisms of genes able to direct the biosynthesis of required proteins. In most cases a protein of interest will normally be synthesized in animal cells and not naturally found in yeasts or other lower eukaryotes. Although it has been possible to clone a number of different animal genes containing the information necessary to code for proteins, reports of the expression of these proteins in bacteria and other unicellular organisms is limited. Some which have been expressed in *E. coli* are the human polypeptide hormone somatostatin [Itakura, K., Hirose, T., Crea, R., Riggs, A. D., Heyneker, H. L., Bolivar, F. and Boyer, H. W. (1977) Science 198: 1056–1063], rat proinsulin, and human insulin chains.

Previously we succeeded in expressing the chicken ovalbumin gene in *E. coli* HB101 by fusing said gene near transcriptional and translational initiation regions. See Proceedings of National Academy of Sciences (1978) 75:5936–5940. Next, we succeeded in expressing the chicken ovalbumin gene in yeast by fusing said gene in the correct orientation relative to a transcriptional initiation region.

BRIEF SUMMARY OF THE INVENTION

Utilizing recombinant DNA methodology, described infra, the bovine growth hormone (bGH) structural gene has been fused to a *S. cerevisiae* transcriptional control region. When a plasmid containing the hybrid gene is introduced into *S. cerevisiae*, a protein identified as bovine growth hormone by immunoreactivity is synthesized.

Bovine growth hormone is a protein of 191 amino acids that is synthesized in the anterior pituitary. The molecular weight of the mature protein is about 22,000 daltons, but it is initially made as a pre-growth hormone, with an extra 26 amino acids on the amino terminal end. This tail is normally cleaved during secretion of the hormone. Administration of exogenous bovine growth hormone increases milk production in cows and may increase meat production.

REFERENCE TO THE DRAWING

The drawing depicts the process steps to make the bGH-fused yeast plasmid pBGH1. Though the abbreviations used are conventional and well known to those skilled in the art, they are redefined here to facilitate a clear understanding of the invention.

Restriction endonucleases: Sal I (in the Examples).
Tc$^r$—tetracycline resistance gene.
amp$^r$—ampicillin resistance gene.
Yeast his 3 gene—gene coding for an enzyme required for the biosynthesis of histidine in yeast.
T4 DNA ligase—enzyme coded for by bacteriophage T4.
YEp—yeast episomal plasmid.
pLG23—plasmid containing bovine growth hormone cDNA.

DETAILED DESCRIPTION OF THE INVENTION

The plasmids YEp6, pLG23, and pBGH1, described herein, have been deposited in *E. coli* hosts in the permanent collection of the Northern Regional Research Laboratory, U.S. Department of Agriculture, Peoria, Ill., U.S.A. Their accession numbers in this repository are as follows:

HB101—NRRL B-11371
HB101 (pLG23)—NRRL B-12436
HB101 (YEp6)—NRRL B-12093
HB101 (pBGH1)—NRRL B-12483.

pBGH1 has also been deposited in *S. cerevisiae* LL20 strain. The accession numbers of these yeast deposits are as follows:

*S. cerevisiae* LL 20 strain—NRRL Y-12484
LL20 (pBGH 1)—NRRL Y-12485.

The above deposits are available to the public upon the grant of a patent. It should be understood that the availability of the deposit does not constitute a license to practice the subject invention in derogation of patent rights granted with the subject instrument by governmental action.

The YEp6 plasmid [Struhl, K., Stinchcomb, D. T., Scherer, S. and Davis, R. W. (1979) Proc. Nat. Acad. Sci. 76: 1035–1039] contains an *E. coli* replication origin and ampicillin resistance marker derived from pBR322 so that it can be maintained in *E. coli*. In addition, it contains a yeast plasmid replication origin and yeast His3 gene so that it can be maintained in his$^-$ yeast auxotrophs. The YEp6 plasmid also has a unique Sal I restriction endonuclease site which can be used for cloning foreign DNA.

Construction of the YEp6-pLG23 fused plasmid, pBGH1, proceeds as shown in the drawing. The YEp6 plasmid is cut with Sal I and the resulting linear molecule is treated, advantageously, with alkaline phosphatase to remove the 5' phosphate groups on the ends of the molecule.

The pLG23 plasmid contains nearly all of the bGH mRNA sequence, including all of the information required to code for the amino acid sequence of bGH. This plasmid is cut with Sal I, ligated with the alkaline phosphatase-treated, Sal I cut YEp6 and transformed into *E. coli*. Transformants are selected on ampicillin plates and their plasmid DNA's analyzed.

Preparations of the plasmid DNA's are made by growth in *E. coli* and used to transform *S. cerevisiae*. His+ transformants are selected on supplemented minimal media plates under conditions where the His$^-$ parents can not grow. The transformants are then grown in broth and lysed. The extracts are analyzed for bGH immunoreactivity with an $^{125}$I radioimmunoassay.

The following examples are illustrative of the process and products of the subject invention but are not to be construed as limiting. All percentages are by weight and all solvent mixture proportions are by volume unless otherwise noted.

EXAMPLE 1

DNA Preparation pLG23 plasmid DNA from NRRL B-12436 is isolated by the salt precipitation technique described by Guerry et al. [Guerry, P., LeBlanc, D. J. and Falkow, S. (1973), J. Bact. 116: 1064-1066]. L-broth[Lennox, E. S. (1955), Virology 1: 190-206] containing 10 μg/ml tetracycline is inoculated with an overnight broth culture of NRRL B-12436. Cultures are shaken vigorously at 37° C. until the optical density at 600 nm reaches 0.8; plasmid copy number is then amplified for 18 hours with chloramphenicol (250 μg/ml). Cells are washed once in 50 mM Tris.HCl, pH 8.0, 20 mM EDTA, and resuspended in 33 ml of 25% sucrose in TE (10 mM Tris.HCl, pH 8.0, 0.1 mM EDTA) per liter of culture. Following the addition of 1 mg/ml lysozyme, the suspension is incubated on ice for five minutes, followed by addition of ⅓ volume of 0.25 M EDTA, pH 8.0 and another 5 minute incubation on ice. Cells are lysed by addition of 10% sodium dodecyl sulfate (SDS) in 37 mM Tris.HCl, pH 8.0, 67 mM EDTA, to a final concentration of 1.3% followed by incubation at 37° C. for 30 minutes.

Chromosomal DNA is salted out by bringing the NaCl concentration to 1 M; followed by cooling at 4° C. overnight. SDS and chromosomal DNA are removed by centrifuging at 17,000×g for 30 minutes at 4° C. The resulting supernatant is ethanol precipitated, pelleted, and redissolved in TE. This material is phenol extracted twice, ether extracted, ethanol precipitated, pelleted and resuspended in TE.

Plasmid DNA is further purified by cesium chloride-ethidium bromide density gradient centrifugation. Cesium chloride is dissolved in the DNA solution at a ratio of 1:1 (wt.:vol.), followed by addition of 550 μg/ml ethidium bromide. Gradients are centrifuged for approximately 40 hours at ca. 100,000×g. Plasmid DNA is removed from the gradient by needle puncture, and the ethidium bromide extracted with $H_2O$-saturated 1-butanol. DNA is then dialyzed in 10 mM Tris.HCl, pH 8.0, 0.1 mM EDTA, followed by a final ethanol precipitation. Purified plasmid DNA is dissolved in 10 mM Tris.HCl, pH 8.0, 0.1 mM EDTA.

If ampicillin is substituted for tetracycline in the method described above for preparing pLG23 DNA, the method can also be used to prepare YEp6 DNA and pBGH1 DNA in E. coli. Other plasmid DNA's can be prepared by this method if an appropriate selection (i.e., another antibiotic) is used to maintain the plasmid in the culture. Also, it is within the skill of those in the art to vary the above conditions to prepare plasmid DNA.

EXAMPLE 2

Restriction Endonuclease Digestions

Sal I digestion of YEp6 DNA and pLG23 DNA, prepared as described in Example 1, is done in a reaction mixture containing 6 mM Tris.HCl, pH 8.0, 6 mM $MgCl_2$, 150 mM NaCl, 6 mM β-mercaptoethanol, 100 μg/ml autoclaved gelatin, 80 μg/ml DNA and 80 units/ml Sal I restriction endonuclease. After incubation for 60 minutes at 37° C., the reaction mixture is phenol extracted, ether extracted and ethanol precipitated. It should be realized that the use of another vehicle might require the use of a different restriction endonuclease.

It is within the skill of those in the art to vary the concentrations of reagents, substrates and enzymes as well as reaction conditions to obtain the desired cleavages.

EXAMPLE 3

Alkaline Phosphatase Treatment

This procedure is carried out essentially as described by Ullrich et al. [Ullrich, A., Shine, J., Chirgwin, J., Pictet, R., Tischer, E., Rutter, W. J., and Goodman, H. M. (1977) Science 196: 1313-1319] with some minor modifications. Twelve units/ml of bacterial alkaline phosphatase (BAPF, Worthington) in 20 mM Tris.HCl, pH 8.0, are pre-incubated at 70° C. for 10 minutes. One hundred μg/ml of Sal I cut YEp6 DNA, prepared as described in Example 2, is then added and incubation at 70° C. continues for 15 minutes. The reaction mixture is then phenol extracted three times, ether extracted, and ethanol precipitated. This procedure is optional in the preparation of pBGH1. However, use of the procedure affords a higher ratio of pBGH1 to parental YEp6 plasmid among ampicillin resistant transformants, thereby facilitating the recovery of pBGH1.

EXAMPLE 4

T4 DNA Ligase

In order to ligate the pLG23 DNA to the alkaline phosphatase treated YEp6 DNA, prepared as described in Example 3, the reaction mixture contains 50 mM Tris.HCl, pH 7.8, 10 mM $MgCl_2$, 20 mM dithiothreitol, 1 mM ATP, 30 μg/ml YEp6 DNA, 6 μg/ml Sal I cut pLG23 and 15 units/ml of T4 DNA ligase. After incubation for 16 hours at 12.5° C., the reaction mixture is ethanol precipitated and the pellet dissolved in TCM (10 mM Tris.HCl, pH 8.0, 10 mM $CaCl_2$, 10 mM $MgCl_2$). It is within the skill of those in the art to vary the concentrations of reagents, substrates and enzymes, as well as reaction conditions, to obtain the desired ligations.

EXAMPLE 5

Transformation of E. coli

One hundred twenty ml. of L-broth (1% tryptone, 0.5% yeast extract, 0.5% NaCl) are inoculated with an 18 hour culture of HB101 NRRL B-11371 and grown to an optical density of 0.6 at 600 nm. Cells are washed in cold 10 mM $MgSo_4$ and resuspended for 15 minutes in 20 ml chilled 50 mM $CaCl_2$. Bacteria are then concentrated to one-tenth of this volume in $CaCl_2$ and mixed 2:1 (v:v) with ligated DNA, prepared as described in Example 4. After chilling the cell-DNA mixture for 15 minutes, it is heat shocked at 42° C. for 2 minutes, then allowed to equilibrate at room temperature for ten minutes before addition of L-broth 2½ times the volume of the cell-DNA suspension. Transformed cells are incubated in broth at 37° C. for one hour before inoculating selective media (L-agar plus 20 μg/ml ampicillin) with 200 μl/per plate. Plates are incubated at 37° C. for 48 hours to allow the growth of transformants. This procedure yields E. coli HB101 (pBGH 1), NRRL B-12483. Although the transformation procedure is essential for the amplification of biochemically constructed recombinant DNA molecules, the choice of conditions for such a procedure can be changed by those skilled in the art to achieve the desired purpose.

The plasmid DNA is isolated from E. coli HB101 (pBGH1), NRRL B-12483, by using the procedures of Example 1. The isolated DNA is then transformed into yeast as disclosed in Example 6, infra.

EXAMPLE 6

Transformation of NRRL Y-12484 to NRRL Y-12485

LL20 strain of Saccharomyces cerevisiae (leu−his−), NRRL Y-12484 is transformed as follows: Twenty ml of log phase culture grown in YEPD broth (1% yeast extract, 2% peptone, 2% glucose) to an $OD_{600}$ of 2.0 ($3 \times 10^7$ cells/ml) were pelleted and resuspended in 1/10 volume 0.9 M sorbitol, 50 mM $KPO_4$ buffer, pH 7.5, 14 mM β-mercaptoethanol. Spheroplasts are formed by addition of 1% Glusulase (Endo Laboratories) and incubation at 30° C. for 60 minutes. After washing three times in 1 M sorbitol, spheroplasts are resuspended in 1/100 original culture volume of 1 M sorbitol, 10 mM Tris.HCl, pH 7.5, 10 mM $CaCl_2$. pBGH1 DNA is added to a final concentration of 20 μg/ml. After incubation at room temperature for 5 minutes, 10 volumes of 40% polyethylene glycol 4000, 10 mM tris.HCl, pH 7.5, 10 mM $CaCl_2$ are added, followed by 10 minutes incubation at room temperature. His+ transformants are selected by overlaying minimal agar [0.7% yeast nitrogen base (Difco), 2% glucose, 2% agarose, supplemented with 20 μg/ml uracil, adenine and tryptophan and 30 μg/ml leucine] with 0.2 ml cells suspended in 10 ml molten (45° C.) regeneration medium (minimal medium containing 1 M sorbitol, 2% YEPD and 3% agarose). Plates are incubated at 28° C. for 5-6 days. Also, it is within the skill of those in the art to vary the above conditions for yeast transformation.

EXAMPLE 7

Yeast Cell Extract Preparation

Yeast cells grown in 100 ml minimal medium at 30° C. to stationary phase are pelleted and resuspended in 10 ml of 1% glusulase (Endo Laboratories) in 1 M sorbitol. The cells are then incubated at 30° C. for 90 minutes and pelleted at 4,000 rpm in a Sorvall HB-4 rotor for 5 minutes. The pelleted shperoplasts ae resuspended in extraction buffer containing 1 mM Tris.HCl, pH 7.4, 1 mM $MgCl_2$, and 50 mM NaCl. The resuspended spheroplasts are then frozen and thawed three times and the cell debris removed by centrifugation. The final protein concentration as determined by absorbance at 280 and 260 nm is approximately 8 mg/ml.

EXAMPLE 8

Radioimmunoassay

The assay is performed in 12×75 mm disposable polypropylene culture tubes. On day one, 400 μl of PBS (phosphate buffered saline) −1% BSA (bovine serum albumin), 100 μl of standard or sample, and 200 μl of diluted anti-bGH serum are added to the tubes. Prior to the assay the antiserum against bGH is diluted 1:400 with 0.05 M EDTA-PBS at pH 7.0, and then diluted to the final working concentration (1:25000) with normal guinea pig serum diluted 1:400 with EDTA-PBS at pH 7.0. The contents of each tube are mixed and incubated at 4° C. for 24 hours. On day two, 100 μl of labeled ($^{125}$I) bGH are added to each tube, the contents are mixed and incubated at 4° C. for an additional 24 hours. On day three, 200 μl of anti-guinea pig gamma globulin serium diluted 1:15 with EDTA-PBS are added to each tube, contents mixed and incubated at 4° C. for an additional 72 hours. On day six, 3 ml of PBS are added to each tube and the tubes are centrifuged at 2500 RPM (1800×g) for 30 minutes. The supernatant is decanted and the precipitate counted for one minute in a gamma counter.

EXAMPLE 9

Other Vehicles, Hosts, and Gene Sources

Examples of other vehicles which can be used in the invention are any that can replicate within yeast, such as YEp2, YEp4, YRp7, YEp20. Also vectors that can replicate in other lower eukaryotic hosts.

Examples of other hosts for the vehicle are any S. cerevisiae derivative or other fungi. It is recognized that these latter hosts would have to be approved by the NIH Guidelines.

EXAMPLE 10

Purification of bGH

The transformed yeast cells of Example 6 are grown in minimal medium [0.7% yeast nitrogen base, 2% glucose, supplemented with 20 mg/ml uracil, adenine and tryptophan, and 30 μg/ml leucine] to early stationary phase, and washed in Dulbecco's phosphate buffered saline (Gibco). The cells, containing bGH, are then resuspended in extraction buffer (1 mM Tris.HCl, pH 7.4, 1 mM $MgCl_2$, 5 mM NaCl) at a ratio of 1:1 (volume in ml: cell weight in g). The cells are then lysed as described in Example 7. Purification to obtain crystalline bGH, for use in the cattle industry or for research purposes, can be done by following the procedures, or obvious modifications thereof, given in the article entitled "Purification of Anterior Pituitary Hormones: Bovine, Rat and Rabbit" by L. E. Reichert, Jr., appearing in the book "Methods In Enzymology," Vol. 37 at p. 360. The book, published in 1975, is available from Academic Press, N.Y.

The use of bGH is disclosed in [Machlin, L. J. (1973) J. Dairy Science 56:575–580; and Bines, J. A., Hart, I. C., and Morant, S. V. (1980) Brit. J. Nutrition 43:179–188].

The work described herein was all done in conformity with physical and biological containment requirements specified in the NIH Guidelines.

We claim:

1. A process for preparing bovine growth hormone which comprises culturing S. cerevisiae LL20 (pBGH1), having the deposit accession number NRRL Y-12485, in an aqueous nutrient medium under controlled conditions.

2. S. cerevisiae LL20 (pBGH1) having the deposit accession number NRRL Y-12485.

3. Plasmid pBGH1.

4. E. coli HB101 (pBGH1), having the deposit accession number NRRL B-12483.

* * * * *